United States Patent [19]
Johnson

[11] Patent Number: 5,520,788
[45] Date of Patent: May 28, 1996

[54] SUPPORT LAYER FOR ENZYME ELECTRODE LAMINATED MEMBRANES

[75] Inventor: Jay M. Johnson, Beavercreek, Ohio

[73] Assignee: The Yellow Springs Instrument Company, Inc., Yellow Springs, Ohio

[21] Appl. No.: 373,596

[22] Filed: Jan. 17, 1995

[51] Int. Cl.$^6$ .................................................. G01N 27/26
[52] U.S. Cl. ........................ 204/415; 204/403; 205/778; 435/14; 435/287.8; 435/817; 435/287.9
[58] Field of Search .................................. 204/403, 415; 435/817, 288, 291

[56] References Cited

U.S. PATENT DOCUMENTS

| | | | |
|---|---|---|---|
| 3,979,274 | 9/1976 | Newman | 204/195 B |
| 4,073,713 | 2/1978 | Newman | 204/195 B |
| 4,484,987 | 11/1984 | Gough | 204/1 T |
| 4,759,828 | 7/1988 | Young et al. | 204/1 T |
| 4,832,797 | 5/1989 | Vadgama et al. | 204/1 T |
| 4,886,740 | 12/1989 | Vadgama | 435/4 |
| 5,352,348 | 10/1994 | Young et al. | 204/153.12 |

FOREIGN PATENT DOCUMENTS

| | | |
|---|---|---|
| 0216577 | 4/1987 | European Pat. Off. . |
| 59-164953 | 9/1984 | Japan . |
| 60-185153 | 9/1985 | Japan . |
| 61-145447 | 3/1986 | Japan . |
| 1442303 | 7/1976 | United Kingdom . |

OTHER PUBLICATIONS

Article "Diffusion Of Protein Molecules Through Membranes Of Controlled Pore Size" Biochemical And Biophysical Research Communications, vol. 5, No. 3, 1961, pp. 196–202, by Eckhardt Fuchs and George Gorin No month available.

Article "Dialysis Studies. III. Modification Of Pore Size And Shape In Cellophane Membranes" by L. C. Craig and Wm. Konigsberg, Rockefeller Institute Laboratories, New York, NY, Aug. 5, 1990 pp. 166–172.

Article "A Physical Interpretation Of The Phenomenological Coefficients Of Membrane Permeability" The Journal Of General Physiology, vol. 45, 1961, by O. Kedem and A. Katchalsky, Weizmann Institute Of Science, Rehovoth, Isreal pp. 143–179 No month available.

Article"Ultrafilter Membranes And Ultrafiltration" John Douglas Ferry, Department of Chemistry, Stanford University, California, Oct. 28, 1935—pp. 373–455—Chemical Reviews, vol. 18, No. 3.

Article "Fractional Dialysis With Cellophane Membranes", Laboratories Of The Rockefeller Institute For Medical Research, New York, NY, Jul. 5, 1956, by Lyman C. Craig and Te Piao King, pp. 4171,4172.

Article "Some Dialysis Epxeriments With Polypeptides" by L. C. Craig and T. P. King—Jul. 11, 1955—Rockefeller Institute For Medical Research, New York, NY—pp. 6620–6624.

Article "Dialysis Studies. II. Some Experiments Dealing With The Problem Of Selectivity" by Lyman C. Craig, Te Piao King and Alfred Stracher, Laboratories Of The Rockefeller Institute For Medical Research—Feb. 6, 1967—pp. 3729–3737.

Article "Restricted Diffusion Of Macromolecules Through Agar–Gel Membranes" by G. K. Ackers and R. I. Steere—Plant Virology Laboratory, Crops Research Div., Agricultural Research Service, Bellsville, MD—Sep. 26, 1961—pp. 137–148.

(List continued on next page.)

*Primary Examiner*—Bruce F. Bell
*Attorney, Agent, or Firm*—Biebel & French

[57] ABSTRACT

Improved Newman type enzyme containing laminated membranes are disclosed for use in conjunction with polarographic cells to measure analyte concentration in solutions. The laminated membranes comprise a semipermeable outer, support layer including super large pores of greater than about 200 Å in diameter. The outer layer preferably comprises pore sizes of about 380–750 Å in diameter and has a percentage porosity of about 0.005–0.2%.

16 Claims, 1 Drawing Sheet

OTHER PUBLICATIONS

Article "Membrane Diffusion Studies With Proteins And Nucleic Acids" Jack Goldstein and Lyman C. Craig, The Rockefeller Institute, New York, NY—Feb. 17, 1960—pp. 1833,1834.

Article "Characterization Of Biological Membranes by Equivalent Pores" by A. K. Solomon, Biophysical Laboratory, Harvard Medical School, Boston, MA—pp. 335–364 No month or year available.

Article "Preparation And Characterization Of Polymeric Membranes Of Graded Porosity" by Harry P. Gregor and Edward Kantner, Mar. 14, 1967, pp. 1169–1171.

Article "On The Permeation Of Cellophane Membranes By Diffusion" by L. B. Ticknor, Apr. 21, 1958—pp. 1483–1485.

Article "Dialysis Studies. VI. Experiments With Amino Acids" by Lyman C. Craig and Allen Ansevin, Laboratories of Rockefeller Institute, New York City, May 20, 1963, pp. 1268–1271.

SUPPORT LAYER FOR ENZYME ELECTRODE LAMINATED MEMBRANES

FIELD OF THE INVENTION

The present invention pertains to an improved laminated membrane structure adapted for use in conjunction with a enzyme electrode.

BACKGROUND OF THE INVENTION

Polarographic cell systems have met with wide acclaim particularly in the medical field, providing for detection and concentration measurement of many desired analytes. Enzymes are commonly used in such systems, especially in those situations wherein the analyte itself is not polarographically active but where a reaction product formed or reactant consumed by an enzymatic reaction with the analyte is polarographically active.

For example, in medical applications, one common procedure is to measure glucose in the blood of a patient. Typically, blood samples are withdrawn from the patient for an in-line analysis for glucose concentration using a glucose oxidase electrode with a polarographic detector for detecting $H_2O_2$ generated in accordance with the reaction:

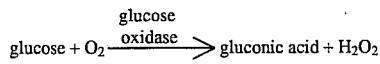

$$glucose + O_2 \xrightarrow{\text{glucose oxidase}} gluconic\ acid + H_2O_2$$

The hydrogen peroxide generated by the reaction is measurable by a polarographic detector and, by appropriate calibration and calculation, glucose content in the sample can be accurately determined by the $H_2O_2$ formed in the reaction.

The polarographic cell systems commonly used for these measurements include an enzyme containing laminated membrane that separates the analyte sample from the working electrode of the cell. These types of membranes are disclosed in the U.S. Pat. Nos. 3,979,274 and 4,073,713 (Newman), both patents being hereby incorporated by reference herein. In such membranes, a thin innermost membrane referred to as a barrier layer composed of cellulose acetate, silicone rubber, or methyl methacrylate is located adjacent the working electrode of the polarographic cell. Glucose oxidase enzyme is interposed between this barrier layer and an outer polycarbonate support layer. The outer support layer is typically about 5 um in thickness and is in contact with the analyte containing sample.

In a glucose analytical determination, glucose and oxygen permeate through the outer support layer and react in the presence of the enzyme. Hydrogen peroxide produced permeates through the inner barrier layer where it is polarographically detected. The support layer permits passage of glucose, oxygen and other molecules therethrough while not permitting passage of high molecular weight substances such as proteins, red blood cells and other macromolecule.

The barrier layer permits access of hydrogen peroxide to the working electrode while blocking passage of substances having molecular weights on the order of about 250 and greater such as ascorbic acid and uric acid.

It has been ascertained that in order to provide accurate linear measurement in solutions containing high glucose concentrations, such as in whole blood or plasma, it is desirable to inhibit diffusion of the glucose to the enzyme layer relative to oxygen migration thereto. Otherwise, the amount of glucose contacting the enzyme exceeds the amount of oxygen available. This makes the oxygen content, rather than the glucose concentration of the sample, the rate limiting component of the reaction. In turn, this leads to inaccurate glucose concentration measurements by the instrument. Linearity, in such situations, occurs only over a range of low glucose concentration. This problem is not only limited to glucose determination but is also experienced in the measurement of other analytes, such as lactate.

In order to overcome this problem, it has been common practice to dilute the glucose and lactate concentrations of the sample so that the as measured analyte concentration level is within the range of concentration exhibiting linearity. However, it is often time consuming and impractical to dilute the analyte containing sample. Additionally, it is becoming commonplace to measure for analytes such as glucose or lactate on a single analytical testing device which incorporates other measurement channels as well. These other channels make use of undiluted whole blood or plasma as the analyte sample input; therefore requiring for uniformity's sake that the glucose and/or lactate measurement channel also function to measure analyte in the same undiluted whole blood or plasma sample medium.

In order to provide accurate glucose or lactate measurement in whole blood, the outer sample contacting membrane layer of the Newman type membranes has been modified to limit diffusion of the analyte to the enzyme layer. For example Japanese patent application Sho 59-40182 disclosed that the pore size of the outer sample contacting membrane should be less than 200 Å or less, with tested 150 Å pore sizes showing improved glucose measurement in whole blood samples. Later, in an obvious variation from the teachings of the Japanese reference, Young et al. in U.S. Pat. 4,759,828 indicated that the outer sample contacting layer should have pore sizes on the order of about 10–125 Angstrom units in diameter. The '828 patent expressly indicates that outer layers of 150 Angstrom unit pore size will not "sufficiently limit the diffusion of glucose molecules to allow glucose measurements to be made on undiluted serum."

In addition to the emphasis placed on small pore sizes in the outer, solution contacting layers of the laminated membrane, Vadgama et al. have emphasized the importance of low porosity materials. Percentage porosity is defined as the product of pore density×pore area×100. Porosities in the range of 0.001% or 0.005% to 0.5% and in general less than 2% are taught in Vadgama et al. E.P. Application 0 216 577.

The move towards use of small pore size support layers has not been without problem. For example, during the fabrication of small pore size films of the type used as outer, solution contacting, layers in laminated enzyme containing membranes, the pores are often formed by an irradiation process in which gamma or other forms of irradiation pierce the solid film precursor to form the desired film pore density. Pore sizes are established in a subsequent etching step using a strong alkali solution. In the final stages of this process, films are washed or treated with high molecular weight surfactants such as polyvinylpyrrolidone.

Poor uniformity has been experienced when these films are incorporated into laminated enzyme containing membranes. It is thought that the large, bulky surfactant molecules used during the film fabrication processes tend to block or clog some of the pores. If this occurs within the relatively small unit area of the film which ultimately is used in a enzyme containing laminated membrane, inaccuracies in analyte determination may be experienced.

Accordingly, there is a need in the art for the provision of an outer layer of an enzyme containing laminated membrane that may be used to measure glucose or lactate in undiluted whole blood or plasma.

There is an even more specific need for the provision of such an outer layer that exhibits enhanced uniformity from one unit area of the film to another so that analyte concentration determination can be made more reliable.

SUMMARY OF THE INVENTION

These and other objects are met by the laminated membranes herein disclosed and claimed. Basically, the invention provides improvement over the membranes disclosed in the aforementioned Newman patents. The improvement resides in the construction of the outer layer or, as it is sometimes referred to, the support layer of the laminated membrane.

Contrary to the teachings in the prior art, it has been discovered that the outer layer of the laminated membrane should be provided with super large pore sizes. These large pores are difficult to block or clog when the film is washed or treated with large surfactant molecules and the like. At the same time, these outer layers function to inhibit glucose or lactate diffusion to the enzyme layer so as to allow for measurement to be made in undiluted whole blood or plasma samples.

The outer semi-permeable membrane layer has pore sizes of greater than about 200 Angstrom units in diameter and exhibits a percentage porosity of from about 0.005–0.2%. The outer layer is preferably composed of polycarbonate polymer, but other materials may be used as long as they have the requisite percentage porosity and pore size. Other exemplary materials include regenerated cellulosics, and polyurethanes.

The invention will be further described in conjunction with the following detailed description read in view of the appended drawing.

DETAILED DESCRIPTION OF THE PREFERRED EMBODIMENT

Figure 1:
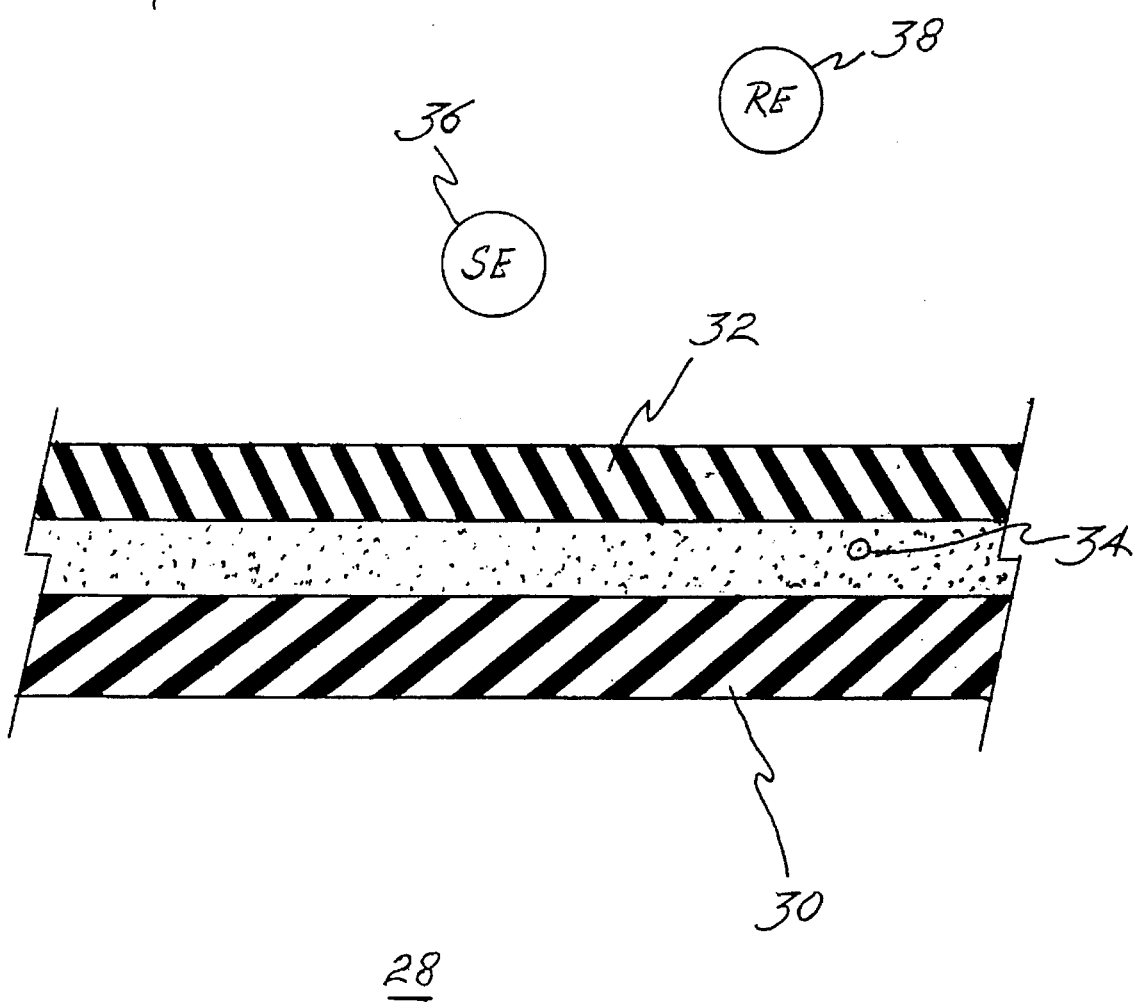
FIG. 1 is an enlarged view of a cross-section of an enzyme containing laminated membrane in accordance with the invention.

With reference to the drawing, there is shown an enlarged cross-section of an enzyme containing laminated membrane 28. Membrane 28 is adapted for use in conjunction with commercially available analytical equipment capable of measuring, for example, glucose or lactate concentration, in undiluted whole blood or plasma solutions.

Barrier layer 32 comprises an homogenous cellulose acetate/cellulose acetate butyrate polymer blend having a thickness of 2 microns or less, preferably 1–2 microns. Enzyme 34 is provided intermediate barrier layer 32 and support layer 30. Enzyme 34 is typically cross-linked in situ between the layers 32, 30 by use of glutaraldehyde although any one of a number of adhesives or cross-linking promoters may be used. Also, it should be mentioned that the enzyme itself may be used as the adhesive without any additional adhesive or cross-linking agent added.

Outer layer or support layer 30, may be comprised of a polycarbonate polymer. It is noted however, that the polymeric identity is not critical provided that layer 30 has pore sizes and a percentage porosity as explained hereinafter. For example, the layer 30 may also comprise polyurethane, regenerated cellulose or other polymer construction. Typically layer 30 will have a thickness of about 5 to 7 microns.

As shown, support layer 30 comprises a single layer. It is to be understood however, that the support layer 30 may actually comprise a multi-layered structure with, for example, bovine serum albumin or other suitable adhesive interposed between layers to yield a composite structure. In this approach pore sizes and individual thicknesses of the layers can be controlled, for instance, to limit or promote migration of a given chemical species to the enzyme 34.

It is to be appreciated that support layer 30 is positioned adjacent the analyte sample and that the barrier layer 32 is therefore adjacent a sensor electrode 36 (typically platinum) in an electrolyte solution. A reference electrode 38 is also disposed in the electrolyte. Accordingly, a polarographic cell is provided in which the electrodes and electrolyte are separated from the analyte solution by the laminated membrane.

As used throughout this disclosure, enzyme 34 will be described as glucose oxidase enzyme. The artisan of course will appreciate that depending on the particular desired analyte and reaction chosen, the enzyme may vary. For instance in analytical situations in which it is desired to monitor lactate levels in blood samples, lactate oxidase will be used as enzyme 34. Other candidate analytes and corresponding oxidoreductase enzymes are noted as being exemplary:

| analyte | oxidoreductase enzyme |
| --- | --- |
| lactose | galactose oxidase |
| sucrose | ( invertase<br>mutarotase<br>glucose oxidase |
| alcohol | alcohol oxidase |
| galactose | galactose oxidase |

Membrane 32 is preferably composed of a blend of cellulose acetate/cellulose acetate butyrate cellulosic esters. The ratio (by weight) of cellulose acetate: cellulose acetate butyrate used to form barrier layer 32 varies widely over a range of 1.5–20:1. Based upon present indications, it is preferred to utilize a 4:1 (by weight) blend of cellulose acetate/cellulose acetate butyrate to cast the film used to form barrier layer 32 of membrane 28.

The requisite ratio of cellulose acetate and cellulose acetate butyrate is dissolved in a two solvent system. The first solvent is a highly volatile organic solvent exhibiting a low boiling point. At present, nitromethane, dimethylformamide and cylcohexanone may be mentioned as being exemplary members of this class of highly volatile organic solvents. All of those have boiling points, under atmospheric conditions, of less than 200° C. At present, it is preferred to use nitromethane as the highly volatile organic solvent.

In addition to use of the volatile solvent, an organic liquid plasticizer is used as a second component of the casting solution. The CA/CAB blend is also soluble in the plasticizer. This plasticizer is characterized by having a boiling point of greater than about 200° C. and must be capable of rendering the CA and CAB compatible (i.e. leading to the formation of a homogenous CA/CAB film). Exemplary organic liquid plasticizers include the phthalates, phosphates, lactones and esters of aliphatic dibasic acids, camphor, etc. Especially preferred are the lactones including γ-butyrolactone and valerolactone. γ-Butyrolactone is presently preferred.

One of the surprising properties of butyrolactone and valerolactone is that they have high boiling points for such tiny molecules.

It is thought that the highly volatile solvent leaves the casting solution quickly while the plasticizer leaves the solution much more slowly and ultimately defines the pores in the layer as it leaves. It is preferred that the plasticizer have a boiling point of about 80° F. higher than the volatile organic solvent. Since the highly volatile organic solvent will leave the solution first, the viscosity of the film increases rapidly enough so that it does not flow or sag appreciably after it is cast. The plasticizer helps to ensure that the cast film maintains its structural integrity with the pores in the film then being defined as it, the plasticizer solvent evaporates.

The first and second solvents can be used in a wide range of addition to the cellulosic esters. The volume ratio of Volatile Organic Solvent:Plasticizer may for instance vary from abut 0.5–1.5 solvent:plasticizer with a ratio of about 1:1 presently preferred.

The volatile organic solvent and plasticizer must be essentially free of high molecular weight impurities, because such impurities would become concentrated as the film dries and would exert an influence on the film out of proportion to their percentage in the starting solvent.

The shape of the plasticizer molecule may also have an influence on pore geometry of the barrier layer. Current wisdom is to the effect that linear molecules move through a film by "reptating" (i.e. a snake-like motion) which can allow the plasticizer to escape through a very irregular or tortuous pore. A substantially spherical molecule such as γ-butyrolactone, on the other hand, has a definite diameter and results in a pore at least equal to that diameter to escape. This suggests that more spherical plasticizer molecules will produce a better-defined pore as they depart from the film.

In addition to the solvent and plasticizer, described supra., a thinner or diluent may be added, as necessary, to accurately control the viscosity of the casting solution. For example, isopropanol, methyl ethyl ketone and ethyl acetate may be mentioned as exemplary. The thinner may be added in an amount by weight of about 0.5–1.5: 1 based on the weight of plasticizer added. Presently, it is preferred to use isopropanol as the thinner, present in amount of 0.88 parts by weight isopropanol: parts by weight plasticizer.

The cellulose esters are added to the highly volatile organic solvent and plasticizer in an amount sufficient to make 10–40 wt.% solutions of (cellulose esters): combined weight of cellulose esters 30 solvent and plasticizer).

The cellulose acetate butyrate (CAB) that is used comprises a mixture of cellulose acetic acid esters and butyric acid esters. Commercially available CABs are graded according to butyryl content of 17, 27, 38, and a 50%. Presently preferred is a CAB product having 28–31% acetyl groups and about 16% butyryl. This product is available from Eastman Kodak.

Turning back now to the construction of the support layer in accordance with the invention, support layer 30 is provided with super large pores. These pores measure at least 200 Angstrom units in diameter. The percentage porosity of layer 30 is within the range of about 0.005–0.200%. Semipermeable films having these properties are available from Poretics, Inc. of Livermore, Calif.

More preferably, layer 30 comprises pores on the order of 380–750 Angstrom units in diameter and a percentage porosity of from about $5\times10^{-2}$ to about $5\times10^{-3}$. Especially preferred is a polycarbonate layer having a pore size of about 450 Angstrom units in diameter and a porosity percentage of about 0.010%.

Examples of permeable porous films useful as layer 30 include those listed in Table I.

TABLE I

| Exemplary Film Characteristics | | |
|---|---|---|
| Pore Size Diameter - Angstrom Units | Pore Density | Percentage Porosity |
| 692 | $6 \times 10^6$ | $2.25 \times 10^{-2}$ |
| 450 | $6 \times 10^6$ | $9.53 \times 10^{-3}$ |
| 382 | $3 \times 10^7$ | $3.6 \times 10^{-2}$ |
| 250 | $3 \times 10^7$ | $1.47 \times 10^{-2}$ |

Based upon presently conducted studies it is preferred to use as support layer 30 a 6 um thick semipermeable polycarbonate film having pore sizes of 450 Å pore density of $6\times10^6$ and a percentage porosity of $9.53\times10^{-3}$.

The following examples are illustrative of the invention and should not be construed to limit the scope thereof.

EXAMPLE ONE

Dextrose containing solutions were injected into a YSI Model 2700 analyzer for glucose concentration measurement utilizing enzyme containing laminated membranes in accordance with the invention. Dilution of the analyte sample at a 20:1 ratio was accomplished internally within this analyzer. For each data point generated six membranes were tested with four dextrose concentration determinations made for each; resulting in 24 determinations for each data point.

A 4% dextrose (40 g/L) solution was chosen to serve as a calibration point. Due to the 20:1 dilution ratio, the resulting dextrose concentration was equivalent to 200 mg %. When these known dextrose solutions were injected into the instrument the following current measurements were obtained:

| | |
|---|---|
| Cal sens (nA) Avg | 19.83 |
| Std. Dev. | 2.62 |

Using the calibration point determined for the 220 mg% dextrose solution, 10% dextrose solution (100 g/L) samples were injected into the Model 2700. Due to the dilution of the sample at a 20:1 ratio within the analyzer, this concentration was equivalent to 500 mg% dextrose. Again 24 test runs (six membranes with four runs per membrane) were made with the resulting dextrose concentrations measured on the Model 2700 as follows:

| 10% dextrose Value (g/L) | (100 g/L) |
|---|---|
| average | 100.91 |
| Std. Dev. | 0.792 |

The membranes used in these tests were laminated glucose oxidase membranes using Poretics Polycarbonate Lot AE66XA91A film as the support layer. Support layer 30 therefore had the following characteristics. Flow rated ® 2.5 m/min./cm² at 10 psi. (450 Angstrom unit pore diameter; pore density=$6\times10^6$ pores/cm²; percentage porosity $9.53\times10^{-3}$).

The results of these tests indicate that the 450 Å super large pore size polycarbonate support layer 30 functioned effectively to measure dextrose (i.e. glucose) within the concentration range of 200 mg %–500 mg % — commensurate with the glucose concentration level found in whole blood.

EXAMPLE TWO

"Poretics" polycarbonate membranes having pore sizes of 692 Angstrom units (diameter), pore density of $6 \times 10^6$ pores/cm$^2$ and a percentage porosity of $2.25 \times 10^{-2}$, are used as a support layer 30 in a glucose oxidase containing laminated membrane of the type shown in the drawing. These laminated membranes are utilized in a YSI Model 2700 analyzer and will measure glucose concentrations over a glucose concentration range of about 200 mg %–500 mg/% glucose.

EXAMPLE THREE

"Poretics" polycarbonate membranes having pore sizes of 382 Angstrom units (diameter), pore density of $3 \times 10^7$ and a percentage porosity of $3.6 \times 10^{-2}$ are used as a support layer 30 in a glucose oxidase containing laminated membrane of the type shown in the drawing. These laminated membranes are utilized in a YSI Model 2700 analyzer and will measure glucose concentrations over a glucose concentration range of 200–500 mg %.

EXAMPLE FOUR

"Poretics" polycarbonate membranes having pore sizes of 250 Angstrom units, pore density of $3 \times 10^7$ pores/cm$^2$ and a percentage porosity of $1.47 \times 10^{-2}$ are used as a support layer 30 in a glucose oxidase containing laminated membrane of the type shown in the drawing. These laminated membranes are utilized in a YSI Model 2700 analyzer and will measure glucose concentrations over a glucose concentration range of 200–500 mg %.

It is accordingly apparent that contrary to conventional wisdom, super large pore size support layers may be used effectively in Newman type laminated membranes. Surprisingly, these support layers are capable of providing accurate analyte concentration measurement even when the analyte is present in high concentration in the sample solutions. These support layers specifically allow for linear, accurate measurement of glucose and lactate in undiluted whole blood and plasma.

Having described the invention in detail and by reference to preferred embodiments thereof, it will be apparent that modifications and variations are possible without departing from the scope of the invention defined in the appended claims.

What is claimed:

1. Laminated membrane for use in a polarographic cell assembly for assay of an analyte in solution, said laminated membrane comprising:

an outer layer having pore sizes of greater than about 200 Angstrom units in diameter and less than about 750 Angstrom units in diameter therein and having a porosity of from about 0.005–0.2%;

an inner layer, and an enzyme layer disposed between said outer layer and said inner layer.

2. Laminated membrane for use in a polarographic cell assembly for assay of an analyte in solution, said laminated membrane comprising:

an outer layer having pore sizes on the order of about 380 to 750 Angstrom units in diameter therein and having a porosity of from about 0.005 to 2%;

an inner layer, and an enzyme layer disposed between said outer layer and said inner layer.

3. Membrane as recited in claim 2, wherein said outer layer has pore sizes of about 450 Angstrom units and wherein said porosity is about 0.010%.

4. Membrane as recited in claim 2 wherein said outer layer has pore sizes of about 692 Angstrom units and wherein said porosity is about 0.0225%.

5. Membrane as recited in claim 2 wherein said outer layer has pore sizes of about 382 Angstrom units and wherein said porosity is about 0.036%.

6. Laminated membrane for use in a polarographic cell assembly for assay of an analyte selected from the group consisting of glucose and lactate in solution, said assembly comprising a reference electrode and a sensor electrode, said laminated membrane positioned proximate said sensor electrode and comprising:

an outer layer of about 5 to 7 microns thick and having pore sizes of greater than about 200 Angstrom units in diameter and less than about 750 Angstroms in diameter and a porosity of from about 0.005–2%;

an inner layer of about 2 microns or less in thickness disposed adjacent said sensor electrode, and an enzyme layer disposed between said outer layer and said inner layer.

7. Membrane as recited in claim 6 wherein said outer layer has pore sizes of about 250 Angstrom units and wherein said porosity is about 0.015%.

8. Laminated membrane for use in a polarographic cell assembly for assay of an analyte selected from the group consisting of glucose and lactate in solution, said assembly comprising a reference electrode and a sensor electrode, said laminated membrane positioned proximate said sensor electrode and comprising:

an outer layer of about 5 to 7 microns thick and having pore sizes of about 380 to 750 Angstrom units in diameter and a porosity of from about 0.005 to 0.2%, said outer layer being composed of a member selected from the group consisting of polycarbonate, regenerated cellulose and polyurethane polymers;

an inner layer of about 2 microns or less in thickness disposed adjacent said sensor electrode, and an enzyme layer disposed between said outer layer and said inner layer.

9. Membrane as recited in claim 8 wherein said outer layer has pore sizes of about 450 Angstrom units in diameter and wherein said porosity is about 0.010%.

10. Membrane as recited in claim 8 wherein said outer layer has pore sizes of about 692 Angstrom units in diameter and wherein said porosity is about 0.0225%.

11. Membrane as recited in claim 8 wherein said outer layer has pore sizes of about 382 Angstrom units in diameter and wherein said porosity is about 0,036%.

12. Laminated membrane for use in a polarographic cell assembly for assay of an analyte in solution, said laminated membrane comprising:

an outer layer comprising a semi-permeable film having pore sizes of about 380–750 Angstrom units in diameter therein;

an inner layer; and an enzyme layer disposed between said outer layer and said inner layer.

13. Laminated membrane as recited in claim 12 wherein said outer layer has pore sizes of about 450 Angstrom units in diameter.

14. Laminated membrane as recited in claim 12 wherein said outer layer has pore sizes of about 692 Angstrom units in diameter.

15. Laminated membrane as recited in claim 12 wherein said outer layer has pore sizes of about 382 Angstrom units in diameter.

16. Laminated membrane as recited in claim 12 wherein said outer layer has a porosity percentage of between about 0.005–0.2%.

* * * * *